US006444462B1

(12) United States Patent
Pfeifer et al.

(10) Patent No.: US 6,444,462 B1
(45) Date of Patent: Sep. 3, 2002

(54) INCUBATION SYSTEM FOR AN ANALYZER APPARATUS

(75) Inventors: John Edward Pfeifer, Redding; William Frederick, Bridgeport; Alvaro Dedios, Norwalk, all of CT (US)

(73) Assignee: Microcensus, LLC, Bethel, CT (US)

( * ) Notice: Subject to any disclaimer, the term of this patent is extended or adjusted under 35 U.S.C. 154(b) by 0 days.

(21) Appl. No.: 09/557,653

(22) Filed: Apr. 25, 2000

(51) Int. Cl.[7] .................................................. C12M 1/38

(52) U.S. Cl. ........................ 435/303.1; 435/3; 435/809; 435/286.1; 422/99; 700/274; 219/428; 219/483; 219/497; 374/1

(58) Field of Search ......................... 435/286.1, 3, 809, 435/303.1; 422/104, 99; 374/1, 3; 219/428, 497, 494, 432, 386, 483; 700/274

(56) References Cited

U.S. PATENT DOCUMENTS

| | | | | |
|---|---|---|---|---|
| 3,586,829 A | * | 6/1971 | Farmer | |
| 3,877,817 A | | 4/1975 | Ralston | 356/180 |
| 3,939,687 A | | 2/1976 | Waldron | 73/1 |
| 3,994,590 A | | 11/1976 | Di Martini | 356/178 |
| 4,027,979 A | | 6/1977 | Komarniski | 356/180 |
| 4,392,746 A | | 7/1983 | Rook et al. | 356/409 |
| 4,475,823 A | | 10/1984 | Stone | 374/1 |
| 5,013,155 A | | 5/1991 | Rybak | 356/408 |
| 5,144,814 A | | 9/1992 | Gaudette | 62/225 |
| 5,307,144 A | | 4/1994 | Hiroshi et al. | 356/244 |
| 5,345,064 A | | 9/1994 | Hesse | 219/505 |
| 5,601,141 A | * | 2/1997 | Gordon et al. | |
| 5,677,134 A | | 10/1997 | Hayashi et al. | 435/7.4 |
| 5,703,342 A | | 12/1997 | Hoffmann et al. | 219/497 |
| 5,770,389 A | | 6/1998 | Ching et al. | 435/7.92 |
| 5,903,346 A | | 5/1999 | Rinke et al. | 356/320 |
| 5,959,738 A | | 9/1999 | Hafeman et al. | 356/440 |
| 6,004,029 A | | 12/1999 | Moslehi et al. | 374/1 |
| 6,010,243 A | | 1/2000 | Hessler et al. | 374/1 |
| 6,106,784 A | * | 8/2000 | Lund et al. | |
| 6,114,674 A | * | 9/2000 | Baugh et al. | |

* cited by examiner

*Primary Examiner*—William H. Beisner
(74) *Attorney, Agent, or Firm*—David P Gordon; David S Jacobson; Thomas A Gallagher

(57) ABSTRACT

An ampoule incubator and light analyzer is provided which includes a housing having at least one receptacle for an ampoule, an incubation system, a light analysis system, and a master control system. According to the invention, the incubation system includes, for each receptacle, a heating element which heats the ampoule and a temperature sensor which senses the temperature of the ampoule. Each receptacle is preferably insulated to prevent unintended heating of neighboring receptacles of the apparatus. The incubation system is adapted to quickly heat the receptacle, and consequently the ampoule provided therein, up to the desired temperature. The incubation system is calibrated by soaking the circuits of the control system in a controlled temperature environment maintained at the desired operation temperature for analysis of the ampoules. When the circuits are at the desired operation temperature, the circuits of the incubation system are powered and switches in the circuits are closed causing a microcontroller of the master control system to store digital representations of the temperature of each individual receptacle in non-volatile memory. Then, during operation of the apparatus, the incubation system is directed to the values previously set in non-volatile memory during calibration, without necessitating expensive and error-prone trim pots, ultra high precision components, or other adjustable components.

19 Claims, 3 Drawing Sheets

INCUBATION SYSTEM FOR AN ANALYZER APPARATUS

BACKGROUND OF THE INVENTION

1. Field of the Invention

This invention relates broadly to analytical instruments. More particularly, this invention relates to an incubation system for an analyzer apparatus.

2. State of the Art

A number of analysis systems require that a test sample under analysis be brought to and held at a desired temperature during analysis. For example, water test kits are used to determine the bacteriological activity within water. According to some kits, a water sample is taken in an ampoule and the ampoule is held at 35° C. Only at the required temperature will the growth of the bacteria be constant so that the sample can be analyzed with light to determine bacteriological content. In the field, some products require that the sample be brought to the required temperature by keeping the ampoule in an inside shirt pocket of the user performing the test. However, this is inexact and inconvenient.

While the prior art does include incubators for other analysis systems, such existing incubators have a number of serious drawbacks. First, many incubators adapted to heat to a particular temperature are quite complex which results in high cost.

Second, complex devices are often bulky. The bulk reduces the portability of the device and inhibits the use of such a device in the field.

Third, incubation systems often require calibration. However, calibration typically requires the use of expensive and adjustable components such as error-prone trim potentiometers or ultra high precision components. Moreover, the adjustment of such components requires the time of the operator and introduces human error.

Fourth, many systems do not permit sample ampoule heating while under analysis. For example, in U.S. Pat. No. 3,877,817 to Ralston, after an ampoule is heated to a desired temperature in a heating compartment, it is then transported to a measuring compartment for analysis as the light source of the light analysis portion of the Ralston system adversely affects proper stabilized heating of the sample ampoule.

SUMMARY OF THE INVENTION

It is therefore an object of the invention to provide an apparatus which maintains ampoules at a desired temperature.

It is another object of the invention to provide an incubation system which is self-calibrating.

It is also an object of the invention to provide a portable and relatively low cost apparatus for heating ampoules.

It is a further object of the invention to provide an apparatus which accurately heats ampoules in the same location at which they are analyzed.

In accord with these objects, which will be discussed in detail below, an ampoule incubator and light analyzer is provided which includes a housing having at least one receptacle (or nest) for an ampoule, a cover for substantially preventing ambient temperature and light from affecting each receptacle, an incubation system, a light analysis system, and a master control system. The incubation system includes, for each receptacle, a heating element which heats the receptacle and a temperature sensor which senses the temperature of the receptacle. Each receptacle is preferably insulated to prevent unintended heating of neighboring receptacles of the apparatus. The light analysis system includes, for each receptacle, at least one light source and a photodetector positioned such that the light from the light source passes through the receptacle (and thereby the ampoule and its contents) prior to entering the photodetector.

The master control system permits user input, operates the incubation system and the light analysis system, and provides a user-readable display for the output of the results of the light analysis of the contents of the ampoule in the receptacle.

According to a preferred aspect of the invention, the incubation system is adapted to quickly heat the receptacle (and consequently the ampoule provided therein) up to the desired temperature. The incubation system is calibrated by soaking the receptacles and associated components including the temperature sensor, all in a powered state on a circuit board, in a controlled temperature environment maintained at the desired operation temperature for analysis of the ampoules, for example, at 35° C. When the receptacles and associated components are at the desired operation temperature, switches are closed causing a microcontroller of the master control system to store digital representations of the temperature of each individual receptacle in non-volatile memory. Then, during operation of the apparatus, the incubation system is directed to the values previously set in the non-volatile memory during calibration, without necessitating expensive and adjustable components such as error-prone trim potentiometers or ultra high precision components, or human intervention during use.

The apparatus may include a large number of receptacles suitable for laboratory use or may include fewer or one receptacle suitable for home or portable use.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 3:
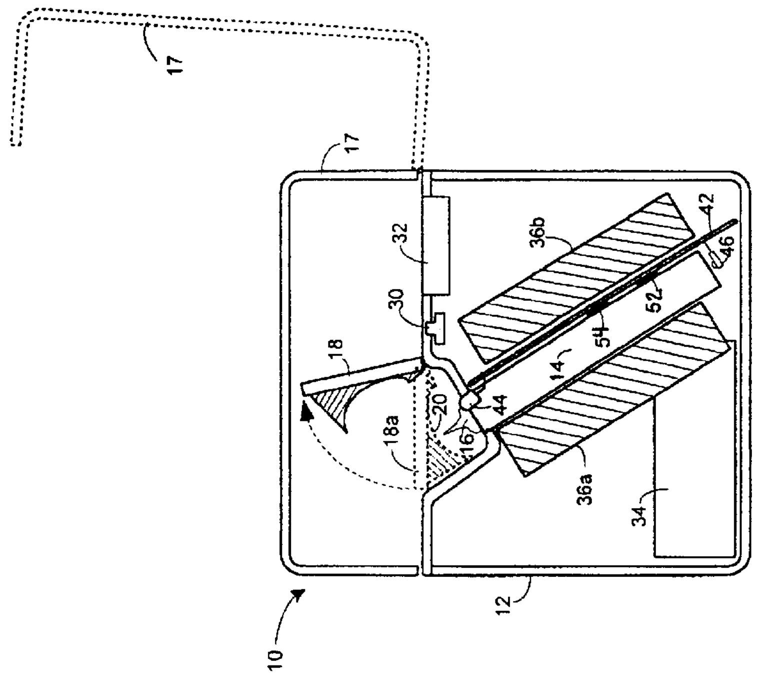
FIG. 3 is a partial side view of the apparatus of the invention showing the case lid in open and closed positions.
Figure 2:
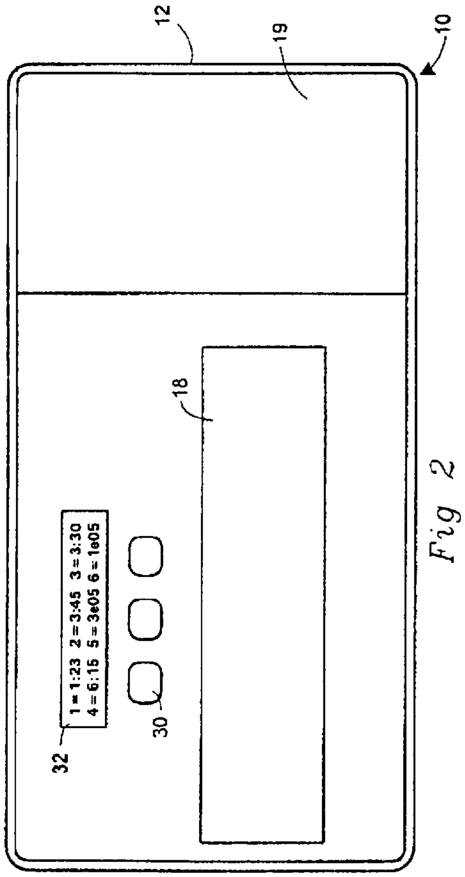
FIG. 2 is a top view of the apparatus of the invention without the case lid.
Figure 1:
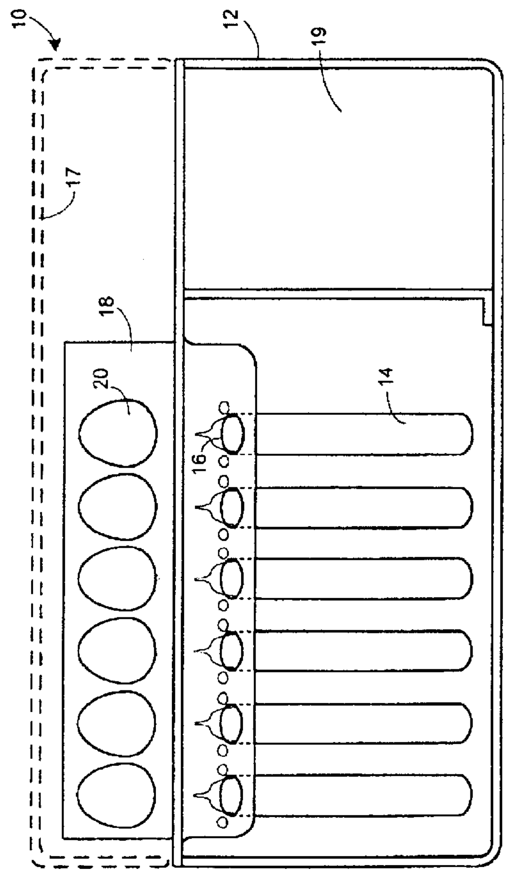
FIG. 1 is a partial front view of the ampoule incubator and light analysis analyzer apparatus of the invention.

Turning now to FIGS. 1 through 3, an ampoule incubator and analyzer 10 according to the invention includes a housing 12 having preferably six receptacles (nests) 14, each for receiving an ampoule 16, and preferably a housing lid 17 movable between closed and open (broken lines) positions. The housing 12 preferably also includes a storage area 19 for storing ampoules. A receptacle cover 18 in an open position provides access to the receptacles and in a closed position 18a substantially prevents ambient light and temperature from affecting each receptacle. The receptacle cover 18 preferably includes a diffuse reflective interior surface 20 which reflects and distributes light from a light source, discussed below, through the receptacles.

Figure 4:
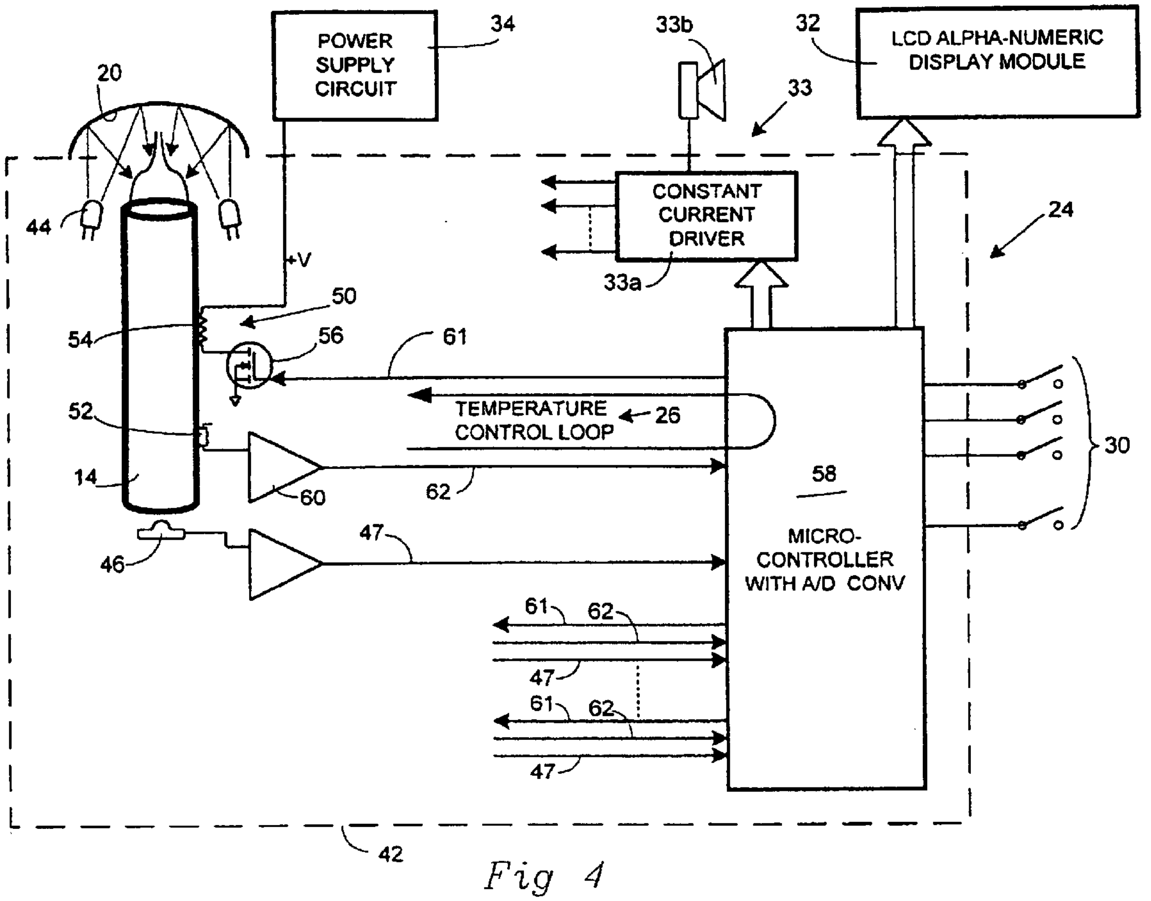
FIG. 4 is a partial schematic circuit diagram of a master control system of the apparatus of the invention.

Referring to FIG. 4, the incubator and analyzer 10 also includes a master control system 24, described in detail below, and, for each receptacle, an incubation system 26 and a light analysis system (not shown generally, though described with respect to the individual elements below). The master control system 24 which includes a microcontroller 58 generally permits user input through control buttons 30, operates the incubation system 26 and the light analysis system 28, and provides information to a user-readable display 32 and a signal to an audio output 33 comprised of a driver chip 33*a* and a sound transducer 33*b* for the output of the results of the light analysis. A power source 34, e.g., a battery and appropriate circuitry to power the various systems is also provided.

Referring to FIG. 3, more particularly, the receptacles 14 are preferably made from a heat conductive material, such as metal and preferably aluminum. Each receptacle is a tube preferably approximately 0.5–0.625 inch in diameter, and preferably approximately four inches in length; i.e., sized to receive a standard water test ampoule. The receptacles 14 are adapted such that when heated they evenly distribute heat around substantially the entire length of ampoules provided therein. Each receptacle 14 is preferably at least partially surrounded by a thermally insulative foam 36*a* to maintain the temperature of the receptacle when heated by the incubation system 26 as described below.

Figure 5:
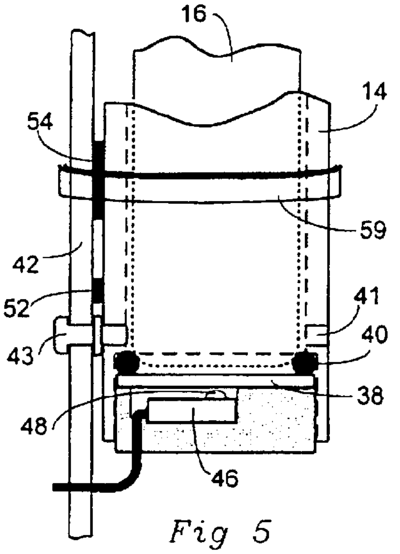
FIG. 5 is a side view of an ampoule receptacle according to the invention.
Figure 6:
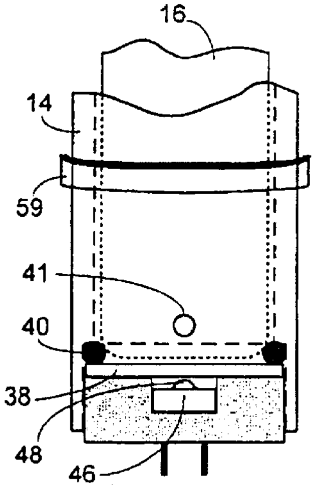
FIG. 6 is a front view of an ampoule receptacle according to the invention.

Turning to FIGS. 5 and 6, a transparent preferably cleanable disk 38, preferably glass or polycarbonate, is provided near a lower end of the receptacle. An O-ring 40 provides a watertight seal between the disk 38 and the interior surface of the receptacle 14. A weep hole 41 is provided in the receptacle adjacent but above the location of the disk 38 to permit any water, test solution, or cleanser which may drip into the receptacle 14 to drain therefrom.

Referring to FIGS. 3 through 6, the receptacles 14 are attached to a printed circuit board (PCB) 42, e.g., by screws 43. The back of the PCB 42 is also provided with an insulative foam 36*b* to facilitate temperature maintenance. For each receptacle, the PCB 42 includes the componentry of the associated incubation system 26 and light analysis system. The light analysis system generally includes a light source 44 adapted to emit light into the receptacle 14 and described in more detail below, and an optical detector 46 providing a signal 47 to the microcontroller 58 and located relative to the light source 44 such that when an ampoule 16 is provided in the receptacle, light emitted by the light source 44 is transmitted through at least a portion of the ampoule and its contents prior to being received by the optical detector 46. Depending on the direction of emission of light by the light source 44 and the relative location of the optical detector 46 (e.g., in an axial transmission where the light source is located near the top of the receptacle and directed generally upwards and the optical detector is located at the bottom of the receptacle), the reflective interior surface 20 of the cover 18 provides desirable light reflectance and scattering through the ampoule 16 toward the detector 46 (FIG. 3). A lens 48 is preferably provided to channel light to the detector 46 (FIGS. 5 and 6). The analysis system preferably functions according to a manner known in the art, such that the contents or a change in the contents is analyzed through photometric or colorimetric means. Such systems are described in various forms and in detail in U.S. Pat. No. 5,959,738 to Hafeman et al., U.S. Pat. No. 5,903,346 to Rinke et al., U.S. Pat. No. 5,770,389 to Ching et al., U.S. Pat. No. 5,307,144 to Hiroshi et al., U.S. Pat. No. 5,013,155 to Rybak, U.S. Pat No. 4,392,746 to Rook et al., U.S. Pat. No. 4,027,979 to Komarniski, U.S. Pat. No. 3,994,590 to Di Martini et al., U.S. Pat No. 3,877,817 to Ralston, which are hereby incorporated by reference herein in their entireties.

As shown best in FIG. 4, the incubation system 26 includes a heating element 50 adapted to heat the receptacle 14 and a temperature sensor chip 52 in contact with the receptacle 14 for determining the temperature thereof. The heating element 50 includes a pack of heater resistors 54 and a driver FET (field effect transistor) 56 which is coupled to a microcontroller 58 of the master control system 24. The temperature sensor chip 52 is preferably a silicon device which produces a voltage related to a sensed temperature. The sensor chip 52 is preferably held tightly against the receptacle 14 to accurately sense the temperature of the receptacle. Preferably one of the screws 43 provides a conductive path from the heat in the receptacle 14 to the temperature sensor 52, and a tie wrap 59 (FIGS. 5 and 6) preferably sandwiches the heater resistors 54 between the PCB 42 and the receptacle 14.

According to a preferred aspect of the invention, the incubation system 26 is calibrated to quickly and accurately heat the receptacle (and consequently the ampoule provided therein) to a desired temperature. The incubation system 26 is calibrated by soaking the PCB 42, with receptacles 14 and incubation system circuitry thereon, in a controlled temperature environment (circulating air bath) maintained at the desired operation temperature for analysis of the ampoules. A preferred temperature for particular samples is 35° C., though other temperatures may be used. The preferred soaking time is preferably approximately twenty minutes to one hour for the receptacle and sensor chip 52 to reach the target (desired operation) temperature. The incubation system 26 is powered during the entire soak and when the components have reached the desired operation temperature, switches in the circuits are closed causing the microcontroller 58 of the master control system 24 to store digital representations (preferably at a resolution of 8 bits; i.e., values 0 to 255) of the temperature of each individual receptacle in non-volatile memory.

Figure 7:
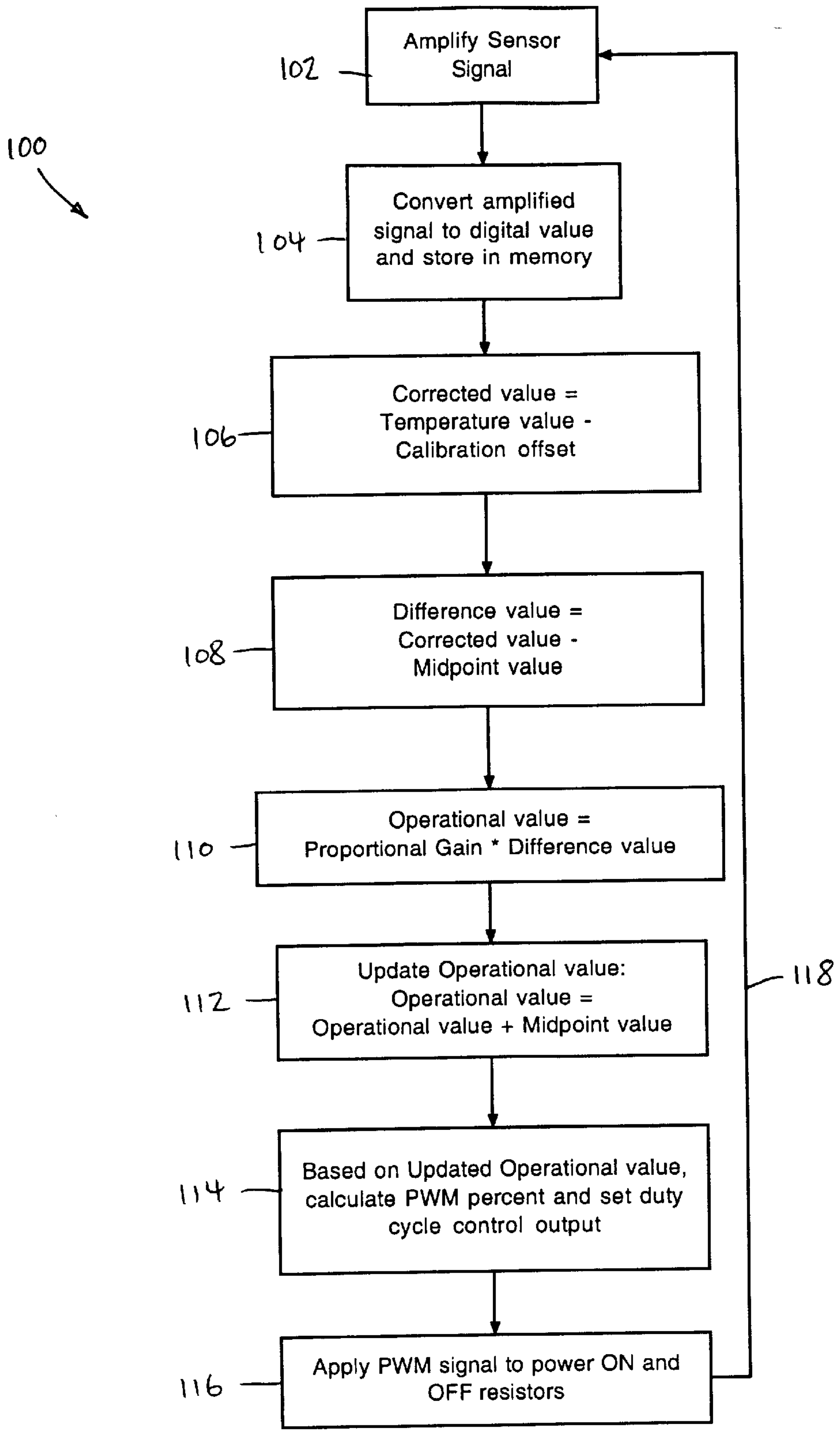
FIG. 7 is a flow chart describing feedback loop operation of the microcontroller during incubation.

Referring to FIGS. 4 and 7, then, during operation of the incubator and analyzer apparatus 10, the incubation system 26 is directed to the values previously set in non-volatile memory during calibration. To that end, proportional control software in the microcontroller 58 implements a feedback loop 100 which brings the receptacle to the desired temperature. More particularly, the sensor signal is preferably amplified at 102 by an amplifier 60 to increase resolution over a limited temperature range, e.g., 30° C. to 50° C., which includes the desired operation temperature. Using the exemplar range, a temperature of 30° C. would be assigned a value of 0, while a temperature of 50° C. would be assigned a value of 255. This provides a resolution of about 20° C. in 255 counts or 0.0784° C. per count. The amplified signal 62 is read by an analog to digital (A/D) converter in the microcontroller 58 and stored at 104 as a value between 0 and 255, corresponding to the temperature reading. After the temperature is read by the A/D converter, a corrected value is determined at 106 by subtracting therefrom the digital value stored during calibration (a calibration offset). The midpoint value (a digital value of 127) is then subtracted from the corrected value to obtain at 108 a difference value (or error). The difference value is then multiplied by a proportional gain to obtain at 110 an operational value. The proportional gain is set by a multiplicative constant which has been empirically determined to be between 6 and 10, and preferably is set at 10. The operational value is then updated at 112 by adding back in the midpoint value. The substraction and addition of the midpoint value at the separate steps allows the numbers to be scaled so that only integer math need be used during the calculations. Based upon the value of the updated operational value, the microcontroller 58 calculates at 114 a pulse width modulation (PWM) percentage and sets a duty cycle control output. In particular, the microcontroller 58 puts out a PWM signal having a period of one second with the duty cycle varied from 0 percent to 100 percent as dictated by the software. If the updated operational value is less than 0, the PWM percent is set to zero. If the updated operational value is greater than the 255 (the maximum), the PWM percent is set to a maximum. If the updated operational value is between 0 and 255, the PWM percent is set to the operational value divided by 255. The PWM signal is applied at 116 as a control signal to control the FET 56 which turns power on and off to the resistors 54 mounted to the receptacle 14. Thus, the duty cycle of the PWM signal adjusts the amount of heat applied to the receptacle. The microcontroller regularly and continuously repeats at 118 the process, bringing the temperature of the receptacle rapidly up to the desired temperature, and then holds the temperature of the receptacle to within approximately 0.1° C. to 0.5° C. of the desired temperature. As such, a very efficient incubation system which requires no calibration and, therefore, no expensive and error-prone trim potentiometers, ultra high precision components, or other adjustable components is provided. Furthermore, the incubation system operates free from human error.

There have been described and illustrated herein an embodiment of an incubation system for an analyzer. While particular embodiments of the invention have been described, it is not intended that the invention be limited thereto, as it is intended that the invention be as broad in scope as the art will allow and that the specification be read likewise. Thus, while a particular feedback loop for the incubator system has been disclosed, it will be appreciated that other feedback loops may be used as well. For example, while the subtraction and addition of the midpoint value in the feedback loop allows the numbers to be scaled so that only integer math need be used during the calculations, this step is not required. Also, while it is desirable to soak all of the printed circuit board, the receptacle, the heating element and the temperature sensor at the desired operation temperature, it will be appreciated that only the temperature sensor need by soaked at the operation temperature, provided that an electrical connection is still maintained with the microcontroller for recording the representation of the temperature. Furthermore, while an 8-bit system has been disclosed to provide the desired resolution, it will be appreciated that a lower or higher resolution system may also be used, with the software updated to appropriately account for the difference. In addition, while the temperature sensor is described as producing a voltage proportional to a sensed temperature, it may alternatively produce a voltage inversely proportional to a sensed voltage, each of which is considered 'proportional' in the claims. Also, while a field effect transistor is preferred as part of the heating element, other transistors, such as a switching transistor, may also be used. In addition, while the receptacles are preferably made entirely from a heat conductive material, it will be appreciated that only elements of the receptacle need be made from a heat conductive material. For example, the receptacle may alternatively include a coiled heating element which resides in the interior of the receptacle and which is in contact with the heating element. In addition, while the apparatus has been described with six independently operable receptacles, the apparatus may include a larger number (e.g., 24 to 36) of receptacles such that it is suitable for laboratory use or may include fewer or one receptacle suitable for home or portable use. Furthermore, while the incubation system has been disclosed with respect to a light analysis system, it will be appreciated that the incubation system may be used with other analysis equipment. It will therefore be appreciated by those skilled in the art that yet other modifications could be made to the provided invention without deviating from its spirit and scope as claimed.

What is claimed is:

1. An incubation system for use with one or more tubular containers, comprising:

a) at least one heat conductive receptacle configured to receive a tubular container and orient the tubular container at an angle relative to horizontal and vertical;

b) for each said receptacle, a heating element attached to said receptacle;

c) for each said receptacle, a temperature sensor in contact with said receptacle which determines a temperature of said receptacle; and d) a microcontroller including software which operates a feedback loop between each said heating element and its associated temperature sensor, causing said heating element to heat its associated receptacle to a desired temperature.

2. An incubation system according to claim 1, wherein:

said heating element includes at least one resistor and a field effect transistor.

3. An incubation system according to claim 1, wherein:

said temperature sensor is a silicon device which produces a voltage proportional to a sensed temperature.

4. An incubation system, comprising:

a) at least one heat conductive receptacle;

b) for each said receptacle, a heating element attached to said receptacle;

c) for each said receptacle, a temperature sensor in contact with said receptacle which determines a temperature of said receptacle;

d) a microcontroller including software which operates a feedback loop between each said heating element and its associated temperature sensor, causing said heating element to heat its associated receptacle to a desired temperature; and e) a printed circuit board to which said at least one receptacle and its associated heating element and temperature sensor are coupled.

5. An incubation system according to claim 4, wherein:

said temperature sensor is sandwiched between said printed circuit board and said receptacle associated with said temperature sensor.

6. An incubation system according to claim 1, wherein:

said microcontroller includes a non-volatile memory storing calibration data.

7. An incubation system according to claim 6, wherein:

said calibration data is a digital representation of a soak temperature at which said at least one temperature sensor is soaked for a period of time.

8. An incubation system according to claim 7, wherein:

said soak temperature is a desired operation temperature of said incubation system.

9. An incubation system according to claim 1, further comprising:

e) thermal insulation about each of said receptacles.

10. A method of calibrating an incubation system, comprising:

a) providing an incubation system including a heat conductive receptacle, a heating element attached to said receptacle, a temperature sensor attached to said receptacle, and a microcontroller coupled in circuit with said heating element and said temperature sensor, b) powering said microcontroller;

c) soaking said incubation system at a predetermined temperature for a period of time; and d) at said predetermined temperature, storing a representation of a reading of said temperature sensor in a non-volatile memory of said microcontroller.

11. A method according to claim 10, wherein:

said soaking is soaking for at least 20 minutes.

12. A method according to claim 10, wherein:

said representation is a digital representation.

13. A method according to claim 10, wherein:

said digital representation is an 8-bit value.

14. A method of heating a device to a desired temperature, said device including a heat conductive receptacle, a heating element attached to said receptacle, a temperature sensor in contact with said receptacle which determines a temperature of the receptacle, and a microcontroller including a non-volatile memory and coupled in circuit with the heating element and the temperature sensor, the temperature sensor having been previously soaked at the desired temperature for a period of time and the microcontroller having been powered to store a calibration value corresponding to a reading of the temperature sensor at the desired temperature in the non-volatile memory of the microcontroller, said method comprising:

a) determining a sensed value corresponding to a sensed temperature;

b) determining a difference between said sensed value and the calibration value;

c) multiplying said difference by a proportional gain to obtain an operational value;

d) based on said operational value, setting a duty cycle control circuit in the microcontroller to output a pulse width modulation (PWM) signal which controls power to the heating element; and e) repeating steps a) through d).

15. A method according to claim 14, wherein:

prior to multiplying said difference by said proportional gain, a difference is updated by subtracting a constant value from said difference, and prior to setting said duty cycle, said operational value is updated by adding said constant value to said operational value.

16. A method according to claim 14, wherein:

said proportional gain is a multiplicative constant between 6 and 10.

17. A method according to claim 14, wherein:

said duty cycle is varied from 0 percent to 100 percent.

18. A method according to claim 14, wherein:

when said updated operational value is less than 0, the duty cycle is set to zero, when said updated operational value is greater than a maximum value of a reading of the temperature sensor, the duty cycle is set to 100 percent, and when said updated operational value is between 0 and said maximum value, the duty cycle is set to the updated operational value divided by said maximum value.

19. A method according to claim 14, wherein:

said sensed value is determined by amplifying said temperature sensor signal over a temperature range which includes the desired temperature, and converting the analog signal to a digital value.

* * * * *